United States Patent
Matsumoto et al.

(10) Patent No.: US 11,253,484 B2
(45) Date of Patent: Feb. 22, 2022

(54) TRANSDERMAL ABSORPTION PREPARATION

(71) Applicant: NITTO DENKO CORPORATION, Ibaraki (JP)

(72) Inventors: Chie Matsumoto, Ibaraki (JP); Tomohito Takita, Ibaraki (JP); Kaiji Fujiwara, Ibaraki (JP); Akinori Sugiyama, Ibaraki (JP); Tomoya Tanaka, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 0 days.

(21) Appl. No.: 16/262,391

(22) Filed: Jan. 30, 2019

(65) Prior Publication Data
US 2019/0231712 A1    Aug. 1, 2019

(30) Foreign Application Priority Data

Jan. 30, 2018 (JP) .............................. JP2018-013614

(51) Int. Cl.
| | |
|---|---|
| A61K 9/70 | (2006.01) |
| A61K 47/12 | (2006.01) |
| A61K 47/18 | (2017.01) |
| A61K 47/36 | (2006.01) |
| A61K 47/32 | (2006.01) |
| A61K 47/38 | (2006.01) |
| A61K 31/197 | (2006.01) |

(52) U.S. Cl.
CPC .......... *A61K 9/7084* (2013.01); *A61K 9/7023* (2013.01); *A61K 31/197* (2013.01); *A61K 47/12* (2013.01); *A61K 47/18* (2013.01); *A61K 47/32* (2013.01); *A61K 47/36* (2013.01); *A61K 47/38* (2013.01)

(58) Field of Classification Search
CPC .......................... A61K 9/7084; A61K 9/7023
See application file for complete search history.

(56) References Cited

U.S. PATENT DOCUMENTS

| | | | | |
|---|---|---|---|---|
| 5,176,916 A | * | 1/1993 | Yamanaka | A61K 9/7053 424/448 |
| 2004/0022835 A1 | | 2/2004 | Pai et al. | |
| 2005/0250804 A1 | * | 11/2005 | Kannan | A61K 9/0014 514/291 |
| 2008/0138388 A1 | | 6/2008 | Aida et al. | |
| 2011/0065627 A1 | * | 3/2011 | Barathur | A61K 31/165 514/1.1 |
| 2011/0150974 A1 | | 6/2011 | Nakajima et al. | |
| 2012/0004305 A1 | | 1/2012 | Miura et al. | |
| 2012/0265158 A1 | * | 10/2012 | Braun | A61K 9/7061 604/307 |
| 2013/0064868 A1 | | 3/2013 | Okazaki et al. | |
| 2013/0064869 A1 | | 3/2013 | Okazaki et al. | |
| 2013/0064875 A1 | | 3/2013 | Okazaki et al. | |
| 2018/0311362 A1 | * | 11/2018 | Takita | A61K 9/703 |

FOREIGN PATENT DOCUMENTS

| | | |
|---|---|---|
| CN | 1509717 A | 7/2004 |
| CN | 102293697 A | 12/2011 |
| CN | 104546808 A | 4/2015 |
| CN | 104547056 A | 4/2015 |
| CN | 105326818 A | 2/2016 |
| CN | 107320716 A | 11/2017 |
| EP | 0156080 A1 | 10/1985 |
| EP | 0436217 A2 | 7/1991 |
| EP | 1731147 A1 | 12/2006 |
| EP | 2407179 A1 | 1/2012 |
| EP | 2777692 A1 | 9/2014 |
| JP | S60-185713 A | 9/1985 |
| JP | H03-209326 A | 9/1991 |
| JP | H07-223938 A | 8/1995 |
| JP | 2000-212078 A | 8/2000 |
| JP | 2013-060393 A | 4/2013 |
| JP | 2013-060394 A | 4/2013 |
| JP | 2013-060395 A | 4/2013 |
| WO | WO 2006/082728 A1 | 8/2006 |

OTHER PUBLICATIONS

Vesey et al., Controlled Release Society Annual Meeting, 2005.*
Woo et al., "Formulation optimization of galantamine hydrobromide loaded gel drug reservoirs in transdermal patch for Alzheimer's disease," *Int. J. Nanomedicine*, 10: 3879-3886 (2015).
European Patent Office, Extended European Search Report in European Patent Application No. 19154547.4 (dated Jul. 8, 2019).

* cited by examiner

*Primary Examiner* — Kyle A Purdy
(74) *Attorney, Agent, or Firm* — Leydig, Voit & Mayer, Ltd.

(57) ABSTRACT

Provided is a transdermal absorption preparation having superior drug skin permeability, which can uniformly disperse the drug in the preparation and maintain the uniform dispersion state of the drug.

A transdermal absorption preparation having a plaster layer containing a drug, a polymer and a pH adjuster, in which the aforementioned polymer contains a polymer having a particular glass transition temperature of 30° C.-200° C., and the surface of the plaster layer has a pH of 6.7-10.0.

12 Claims, No Drawings

TRANSDERMAL ABSORPTION PREPARATION

TECHNICAL FIELD OF THE INVENTION

The present invention relates to a transdermal absorption preparation showing promoted skin permeability of drugs.

BACKGROUND OF THE INVENTION

Adhesive preparations including transdermal absorption preparations not only intend to treat lesions on the skin surface or in the tissues directly under skin application site by topical absorption of the drug, but are also used as preparations expected to act systemically rather than on the skin and nearby tissues by being taken into the blood from subcutaneous blood vessels. They have been recognized as one of the drug delivery systems.

To improve skin permeability of a drug in a transdermal absorption preparation to be adhered to the skin for percutaneous absorption of the drug, the plane area of the preparation needs to be increased. However, when the flat plane area of the preparation is large, handling problems (difficult adhesion to the skin etc.) and problems of skin irritation such as stuff, itching sensation and the like after application to the skin occur. When an adhesive preparation is adhered to a different site, problems that a wide adhesion area is difficult to obtain and the like are present. To improve skin permeability without increasing the flat plane area of the preparation, attempts have been made in conventional transdermal absorption preparations to study transdermal absorption preparations for realizing good skin permeability by including a permeation promoter in the preparation or increasing the drug concentration of the preparation (patent documents 1-4 etc.).

However, some transdermal absorption preparation fails to show sufficient skin permeability by only including a permeation promoter in the preparation, or when the drug concentration of the preparation is increased, it is sometimes difficult to uniformly disperse and maintain the drug in the preparation. Thus, further improvement of transdermal absorption preparations is desired.

DOCUMENT LIST

Patent Documents

[patent document 1] JP-A-2013-060393
[patent document 2] JP-A-2013-060394
[patent document 3] JP-A-2013-060395
[patent document 4] JP-A-60-185713

SUMMARY OF THE INVENTION

Problems to be Solved by the Invention

Therefore, the present invention aims to provide a transdermal absorption preparation that shows superior skin permeability of a drug and can uniformly disperse and maintain the drug in the preparation.

Means of Solving the Problems

The present inventors have conducted intensive studies in an attempt to solve the above-mentioned problems and found that an adhesive preparation having a plaster layer containing a drug, a polymer and a pH adjuster, in which the aforementioned polymer includes a polymer having a particular glass transition temperature, and a surface of the plaster layer has a particular pH range, can realize a transdermal absorption preparation that shows superior skin permeability of a drug and can uniformly disperse and maintain the drug in the preparation, which resulted in the completion of the present invention.

That is, the present invention relates to the following.

[1] A transdermal absorption preparation having a plaster layer containing a drug, a polymer having a glass transition temperature of 30° C.-200° C., and a pH adjuster, wherein a surface of the plaster layer has a pH within a range of 6.7-10.0.
[2] The transdermal absorption preparation of [1], wherein the pH adjuster is an organic acid and/or an organic base.
[3] The transdermal absorption preparation of [2], wherein the organic acid is a fatty acid having 4-20 carbon atoms and the organic base is an aliphatic amine having 4-12 carbon atoms.
[4] The transdermal absorption preparation of any of [1] to [3], further comprising a substrate or a cover material, or a substrate and a cover material laminated on the plaster layer.
[5] The transdermal absorption preparation of any of [1] to [4], further comprising a skin adhesion layer.
[6] The transdermal absorption preparation of any of [1] to [5], which is in the form of a sheet.

Effect of the Invention

According to the present invention, a transdermal absorption preparation that shows superior skin permeability of a drug and can uniformly disperse and maintain the drug in the preparation can be provided.

DESCRIPTION OF EMBODIMENTS

The transdermal absorption preparation of the present invention is a transdermal absorption preparation having a plaster layer containing a drug, a polymer having a glass transition temperature of 30° C.-200° C., and a pH adjuster, and is mainly characterized in that a surface of the plaster layer has a pH range of 6.7-10.0.

The "transdermal absorption preparation" in the present invention refers to a preparation used by closely adhering to the skin, and is preferably provided in the form of a sheet, mainly an adhesive preparation such as a tape preparation (e.g., plaster, etc.), cataplasm and the like.

The transdermal absorption preparation of the present invention has a plaster layer containing a drug, a polymer having a glass transition temperature of 30° C.-200° C. and a pH adjuster, and is preferably formed as a sheet-like transdermal absorption preparation.

The drug to be contained in the transdermal absorption preparation of the present invention is not particularly limited, and any can be used as long as it can maintain good preservation stability in the plaster layer. Examples thereof include general anesthetic, antipsychotic agent, antidepressant, mood stabilizer, psychostimulant, sleeping drug, antianxiety drug, antiepileptic, therapeutic drug for migrainea, antiemetic, anti-vertiginous drug, local anesthetic, muscle relaxant, autonomic drug, antiepileptic drug, therapeutic drug for Parkinson's disease, anti-dementia drug, adrenal cortical steroid, non-steroidal antiinflammatory agent, analgesic antipyretic drug, therapeutic drug for neuropathic pain, antirheumatic drug, anti-histamine drug, antiallergic agent, cardiotonic drug, antiarrhythmic drug, diuretic, depressor, vasoconstrictor, vasodilator, therapeutic drug for angina pectoris, anapnoic, bronchodilator, therapeutic drug for bronchial asthma, antitussive, expectorant, hormone drug, hematopoietic drug, hemostat, antithrombotic, therapeutic drug for gout-hyperuricemia, therapeutic drug for diabetes, therapeutic drug for hyperlipidemia, antitumor drug, immunosuppressant, antibiotic, chemotherapy drug, antifungal agent, antiviral drug, antiparasitic agent, narcotic, narcotic analgesics, non-narcotic analgesics, quit-smoking drug and the like.

Examples of the drug preferably used in the present invention include analgesic antipyretic drug, therapeutic drug for neuropathic pain, non-narcotic analgesics, narcotic analgesics, antipsychotic agents, anti-dementia drug and the like.

The above-mentioned drugs can be contained in a suitable form such as a free form, form of a salt with an acid or base and the like.

Examples of the salts of the above-mentioned drugs include alkali metal salts such as sodium salt, potassium salt and the like; alkaline earth metal salts such as magnesium salt, calcium salt and the like; inorganic acid salts such as hydrochloride, nitrate, sulfate and the like; organic acid salts such as acetate, octanoate, citrate, fumarate, maleate and the like; salts with inorganic base such as ammonium salt and the like; salts with organic base such as triethanolamine salt, pyridine salt, arginine salt and the like, and the like.

The above-mentioned drug and a salt thereof can be produced according to a production method known per se.

The coefficient of partition of the drug to be used in the present invention (1-octanol/water), i.e., log Pow, is preferably −3 to 3, more preferably −2 to 2, further preferably −1 to 2. A drug having a log Pow of to 3 is superior in the drug dispersibility in the plaster layer.

As used herein, the log Pow is an index showing hydrophilicity or hydrophobicity of a drug. It refers to a value measured for each drug by the method described in "OECD GUIDELINE FOR THE TESTING OF CHEMICALS 107, Adopted by the Council on 27 Jul. 1995, Partition Coefficient (n-octanol/water), Shake Flask Method", wherein the base of the logarithm of log Pow is 10. In this embodiment, log Pow was calculated using log P calculation software (Scigress manufactured by FUJITSU). For measurement (calculation) of log Pow, the structural formula of the compound is input to the calculation software and log Pow is calculated.

While the content of a drug in the transdermal absorption preparation of the present invention varies depending on the kind of the drug, the age, sex, symptom of patients to whom the transdermal absorption preparation is used, and the like, it is generally 10 wt %-90 wt %, preferably 20 wt %-70 wt %, of the total amount of the plaster layer.

The polymer in the transdermal absorption preparation of the present invention is a polymer having a glass transition temperature of 30° C.-200° C. A polymer having a glass transition temperature of 30° C.-200° C. is rigid. The presence of these polymers in the plaster layer affords a transdermal absorption preparation capable of maintaining the drug in the preparation in a uniform dispersion state.

For the object of the present invention, the polymer having a glass transition temperature of 30° C.-200° C. preferably has a glass transition temperature of 50° C.-200° C., more preferably 60° C.-180° C.

In the present invention, the "glass transition temperature" means a temperature at which the rigidity and viscosity decrease rapidly and the flowability increases when an amorphous solid is heated. The glass transition temperature of a polymer can be measured by differential scanning calorimeter (DSC) and the like.

Examples of the polymer having a glass transition temperature of 30° C.-200° C. include cellulose derivatives such as hydroxypropylmethylcellulose (e.g., "HPC-M (trade name)", manufactured by NIPPON SODA CO., LTD.), hydroxypropylmethylcellulose phthalate, hydroxypropylcellulose, acetyl cellulose and the like; pullulan "pullulan (trade name)", manufactured by Hayashibara Biochemical Laboratories, Inc.); acrylic polymers such as acrylic resin, methacrylic acid-methyl methacrylate copolymer (methacrylic acid copolymer S ("EUDRAGIT (registered trade mark) S100"), methacrylic acid copolymer L ("EUDRAGIT (registered trade mark) L100"), manufactured by Evonik Rohm GmbH), methacrylic acid-ethyl acrylate copolymer (dried methacrylic acid copolymer LD ("EUDRAGIT (registered trade mark) L100-55", manufactured by Evonik Rohm GmbH)), methyl methacrylate-butyl methacrylate-dimethylaminoethyl methacrylate copolymer (aminoalkyl methacrylate copolymer E ("EUDRAGIT (registered trade mark) EPO", manufactured by Evonik Rohm GmbH)), methyl methacrylate-ethyl acrylate-trimethylammonioethyl methacrylate chloride copolymer (ammonioalkyl methacrylate copolymer ("EUDRAGIT (registered trade mark) RSPO", "EUDRAGIT (registered trade mark) RLPO", manufactured by Evonik Rohm GmbH)), ethyl acrylate-methyl methacrylate copolymer (ethyl acrylate-methyl methacrylate copolymer dispersion solution ("EUDRAGIT (registered trade mark) NE30D", manufactured by Evonik Rohm GmbH)) and the like; polyvinylpyrrolidone; vinylpyrrolidone-vinyl acetate copolymer; polycarbonate; cycloolefin copolymer; polyvinyl caprolactam-polyvinyl acetatepolyethylene glycol graft copolymer ("Soluplus") (registered trade mark), manufactured by BASF); poly(vinyl alcohol); polyvinyl acetate and the like. One or more kinds thereof can be used.

Among these, water-soluble polymers such as cellulose derivatives such as hydroxypropylmethylcellulose, hydroxypropylmethylcellulose phthalate, hydroxypropylcellulose, acetyl cellulose and the like; pullulan; water-soluble acrylic resin; polyvinylpyrrolidone; polyvinyl caprolactam.polyvinyl acetate.polyethylene glycol graft copolymer ("Soluplus" (registered trade mark), manufactured by BASF); poly(vinyl alcohol) and the like, acrylic polymers having pH dependent solubility such as methacrylic acid-methyl methacrylate copolymer (methacrylic acid copolymer S ("EUDRAGIT (registered trade mark) S100"), methacrylic acid copolymer L ("EUDRAGIT (registered trade mark) L100"), manufactured by Evonik Rohm GmbH), methacrylic acid-ethyl acrylate copolymer (dried methacrylic acid copolymer LD ("EUDRAGIT (registered trade mark) L100-55", manufactured by Evonik Rohm GmbH)), methyl methacrylate-butyl methacrylate-dimethylaminoethyl methacrylate copolymer (aminoalkyl methacrylate copolymer E ("EUDRAGIT (registered trade mark) EPO", manufactured by Evonik Rohm GmbH)), and the like are preferably used.

In the present invention, "water-soluble" means being dissolved or dispersed in water at a concentration of not less than 1 wt %. As the aforementioned polymer having pH dependent solubility, a polymer having water solubility at a pH of 6.7-10.0 is more preferably used.

Among the above-mentioned polymers, particularly, hydroxypropylmethylcellulose, hydroxypropylmethylcellulose phthalate, hydroxypropylcellulose, acetyl cellulose and the like cellulose derivative, pullulan, methacrylic acid.m- ethyl methacrylate copolymer, and methacrylic acid.ethyl acrylate copolymer are further preferably used.

The content of the polymer having a glass transition temperature of 30° C.-200° C. is 5 wt %-70 wt %, preferably 10 wt %-50 wt %, relative to the total amount of the plaster layer.

The plaster layer may further contain a polymer other than the polymer having a glass transition temperature of 30° C.-200° C. As such polymer, a polymer having a glass transition temperature of not less than −100° C. and less than 30° C. is preferable and, for example, an adhesive such as acrylic adhesive, silicone adhesive, rubber adhesive and the like can be used. The content of the polymer is preferably less than 100 parts by weight, more preferably not more than 80 parts by weight, further preferably not more than 60 parts by weight, furthermore preferably not more than 40 parts by weight, particularly preferably not more than 20 parts by weight, most preferably 0 part by weight; per 100 parts by weight of the polymer having a glass transition temperature of 30° C.-200° C.

The pH regulator in the transdermal absorption preparation of the present invention may be any compound as long as it is an acid or a base or a salt thereof generally used for adjusting pH. For example, inorganic substances such as hydrochloric acid, sulfuric acid, phosphoric acid, hydroxide of alkali metal, hydroxide of alkaline earth metal, carbonate, hydrogen carbonate and the like; organic acids such as acetic acid, methanesulfonic acid, oxalic acid, caprylic acid, pelargric acid, capric acid, lauric acid, myristic acid, palmitic acid, stearic acid, isostearic acid, oleic acid, glycolic acid, lactic acid, malic acid, tartaric acid, citric acid, levulinic acid, fumaric acid, maleic acid and the like; organic bases such as ethylamine, diethylamine, triethylamine, monoethanolamine, diethanolamine, triethanolamine, monoisopropanolamine, diisopropanolamine, triisopropanolamine, lysine, arginine and the like; and the like can be used as pH regulators.

The content of the pH regulator in the present invention is preferably 20 wt %-70 wt %, more preferably 40 wt %-60 wt %, relative to the total amount of the plaster layer. The content of the pH regulator in the plaster layer of the present invention can be appropriately adjusted according to the numerical value range of the surface of the plaster layer pH.

Examples of the organic acid used as the pH regulator in the present invention include straight chain or branched chain fatty acid preferably having 4-20, more preferably 10-20, carbon atoms. Examples of such fatty acid include capric acid, lauric acid, myristic acid, palmitic acid, stearic acid, isostearic acid, oleic acid and the like. Further preferred are capric acid and oleic acid.

Preferable examples of the organic base used as the pH regulator in the present invention include aliphatic amine having 4-12 carbon atoms. Examples of such aliphatic amine include ethylamine, diethylamine, triethylamine, monoethanolamine, diethanolamine, triethanolamine, monoisopropanolamine, diisopropanolamine, triisopropanolamine and the like. Further preferred are monoethanolamine, diethanolamine, triethanolamine, monoisopropanolamine, diisopropanolamine and triisopropanolamine.

The content of the organic acid is preferably 10 wt %-50 wt %, more preferably 20 wt %-40 wt %, relative to the total-amount of the plaster layer.

The content of the organic base is preferably 5 wt %-40 wt %, more preferably 10 wt %-30 wt %, relative to the total amount of the plaster layer.

The content ratio of the organic acid and organic base in the plaster layer can be appropriately adjusted according to the numerical value range of the surface of the plaster layer pH.

For the object of the present invention, it is preferable that the surface of the plaster layer has a pH range of 6.7-10.0, preferably 7.0-9.8. When the pH range of the surface of the plaster layer is 6.7-10.0, superior skin permeability of a drug can be achieved without a fear of causing skin inflammation and the like. The pH of the surface of the plaster layer can be measured by the method described in the below-mentioned Example.

In the present invention, it is preferable to adjust the pH of the surface of the plaster layer to the numerical value of pH at which a polymer having a glass transition temperature of 30° C.-200° C. dissolves. This is considered to make the body fluid and the like on the skin promote dissolution of the polymer and the like constituting the plaster layer and improve releasability of the drug in the plaster layer.

In the present invention, the plaster layer can contain additives widely used for transdermal absorption preparation such as tackifier, crosslinking agent, excipient, antioxidant, preservative and the like as long as the characteristics of the present invention are not impaired.

While the thickness of the plaster layer is not particularly limited, it is preferably not less than 0.1 µm, more preferably not less than 1 µm, from the aspect of handling during production. Also, from the aspect of the transdermal absorbability of drug, it is preferably not more than 1,000 µm, more preferably not more than 500 µm.

In the transdermal absorption preparation of the present invention, a substrate or a cover material, or both a substrate and a cover material can be laminated on the plaster layer.

The material of the above-mentioned substrate is not particularly limited, and a preferable material is one that does not allow a drug contained in the plaster layer to pass through the substrate and get lost from the back face to decrease the content, namely, one constituted of a material impermeable to the drug. Examples thereof include single films of polyester-based resins such as polyethylene terephthalate) and the like; polyamide-based resins such as nylon and the like; olefin-based resins such as polyethylene, polypropylene and the like; vinyl-based resins such as ethylene-vinyl acetate copolymer, polyvinyl chloride, polyvinylidene chloride, ionomer resin and the like; acrylic resins such as ethylene-ethyl acrylate copolymer and the like; fluorocarbon resins such as polytetrafluoroethylene and the like; metal foil and the like, and these laminate films and the like.

The thickness of the substrate is generally 10 µm-200 µm, preferably 15 µm-150 µm, more preferably 20 µm-100 µm.

To improve adhesiveness (anchor property) between the substrate and the plaster layer, it is preferable that the substrate is a laminate film of a non-porous film and a porous film, each made of the above-mentioned materials, and the plaster layer is adhered to the porous film side of the laminate.

The aforementioned porous film is not particularly limited as long as the anchor property between the substrate and the plaster layer is improved. Examples thereof include paper, woven fabric, non-woven fabric, mechanically perforation-treated film and the like, particularly paper, woven fabric and non-woven fabric are preferable. The thickness of the porous film is preferably 10 µm-100 µm in consideration of the improvement of the anchor property and flexibility of the plaster layer. When woven fabric or non-woven fabric is used as a porous film, the amount thereof is preferably set to 3 g/m²-50 g/m², more preferably 5 g/m²-30 g/m², to improve anchor property.

The cover material is generally formed to have a larger planar shape than the planar shape of the plaster layer. To adhere or closely adhere the plaster layer to the skin, the cover material is laminated on the plaster layer or on the above-mentioned substrate laminated on the plaster layer.

Therefore, the cover material generally has a skin surface adhesive layer formed on a support.

As a support constituting the cover material, a single film of a resin and the like similar to those used for the substrate, or a laminate film thereof, or these films laminated with woven fabric, non-woven fabric and the like can be used. Of these, one maintaining skin followability, that is, one easily expanding and/or contracting according to the elongation of the skin surface is preferable. For example, single films and laminate films of thermoplastic resins such as poly(ethylene terephthalate), nylon, polyethylene, polypropylene, ethylene-vinyl acetate copolymer, polyvinyl chloride, polyvinylidene chloride, ionomer resin and polytetrafluoroethylene, and these films laminated with woven fabric or non-woven fabric are preferably used.

As a skin surface adhesive layer in the cover material, an adhesive layer can be formed from an adhesive similar to the adhesive contained in the below-mentioned skin adhesion layer, such as acrylic adhesive, rubber adhesive, silicone adhesive, vinyl ether adhesive and the like.

The skin surface adhesive layer can also be formed from a material similar to the so-called hydrocolloid dressing material. Specifically, it can be formed from a mixed dispersion of an elastomer component and a hygroscopic substance.

Examples of the elastomer component include polyisobutene, polyisoprene, acrylic polymer, styrene-isoprene-styrene block copolymer and the like. One or more kinds of these can be used. In addition to these, polybutadiene, styrene-butadiene-styrene block copolymer, natural rubber, silicone polymer using polymethylsiloxane or the like as the main component, polyvinyl ether polymer and the like can be used.

The hygroscopic substance is not particularly limited, and any component can be used as long as it can impart liquid absorbability to the skin surface adhesive layer. Specifically, sodium carboxymethylcellulose, dextrin, pectin, gelatin and the like can be mentioned, and one or more kinds thereof can be used. In addition to these, calcium carboxymethylcellulose, hydroxypropylcellulose, guar gum, locust bean gum, xanthan gum, sodium alginate, calcium alginate, carrageenan, collagen, polyvinylpyrrolidone and the like can also be used.

Furthermore, the skin surface adhesive layer can also be formed from a moistening adhesiveness composition.

Such moistening adhesiveness composition can be formed as a jelly composition containing a film forming agent such as poly(vinyl alcohol) and the like, a thickener such as sodium carboxymethylcellulose, carboxyvinyl polymer and the like, moisturizer such as propylene glycol, glycerol, sorbitol and the like, or a paste composition further containing a powder such as titanium oxide, kaolin and the like.

The below-mentioned release liner can be laminated on the skin surface adhesive layer of the cover material to protect the surface to be adhered to the skin until use.

In the present invention, moreover, a skin adhesion layer can be further laminated on the plaster layer. It is preferable to laminate a skin adhesion layer to improve adhesiveness to the skin whet the plaster layer has low skin adhesiveness.

As an adhesive used to form a skin adhesion layer, adhesives widely used for transdermal absorption preparations to be adhered to the skin can be used without particular limitation. For example, acrylic adhesives such as acrylic copolymer of 50-99 wt % of alkyl (meth)acrylate having an alkyl group having 4-12 carbon atoms, and 1-50 wt % of a functional group-containing monomer (e.g., carboxyl group-containing monomer such as (meth)acrylic acid, maleic acid, maleic anhydride and the like, hydroxyl group-containing monomers such as hydroxyethyl (meth)acrylate, hydroxypropyl (meth)acrylate and the like, sulfo group-containing monomers such as styrenesulfonic acid, allylsulfonic acid, sulfopropyl (meth)acrylate and the like, and the like) and the like; styrene-diene-styrene block copolymer (e.g., styrene-isoprene-styrene block copolymer, styrene-butadiene-styrene block copolymer and the like); rubber adhesives such as polyisoprene, polyisobutene, butyl rubber, polybutadiene and the like; silicone adhesives such as silicone rubber, dimethylsiloxane based, diphenylsiloxane based and the like; vinyl ether adhesives such as polyvinyl methyl ether, polyvinyl ethyl ether, polyvinyl isobutyl ether and the like; vinyl ester adhesives such as vinyl acetate-ethylene copolymer and the like; polyester adhesives composed of a carboxylic acid component such as dimethyl terephthalate, dimethyl isophthalate, dimethyl phthalate and the like and a polyhydric alcohol component such as ethylene glycol and the like, and the like. From the aspect of skin adhesiveness, a water-free adhesive is preferable.

The "water-free adhesive" here is not necessarily limited to one completely free of water, and one containing humidity in the air or a slight amount of water derived from the skin and the like is encompassed therein. The "slight amount of water" here is preferably not more than 5 wt %, more preferably not more than 2 wt %, most preferably not more than 1 wt %, as the water content of a laminate of a support and an adhesive layer.

The "water content of a laminate of a support and an adhesive layer" here means a weight ratio of water contained in the laminate of the support and the adhesive layer (water content (weight percentage) relative to the total weight of the laminate of the support and the adhesive layer). When a release liner is present, the release liner is detached and the water content is measured with a Karl Fischer moisture meter by the coulometric titration method. To be specific, for example, a transdermal absorption preparation to be the sample is punched out in a given size under an environment controlled to temperature=23±2° C. and relative humidity=40±5% RH to produce a test piece. Thereafter, when the test piece has a release liner, the release liner is removed and the piece is cast into a water evaporation apparatus. The test piece is heated in the water evaporation apparatus at 140° C., the water moisture generated thereby is introduced into a titration flask using nitrogen as a carrier and the water content (wt %) of the sample is measured by the Karl Fischer coulometric titration method.

The above-mentioned adhesive may be crosslinked as necessary by a physical crosslinking treatment by UV radiation, radiation irradiation (e.g., electron beam irradiation etc.) and the like or a chemical crosslinking treatment using various crosslinking agents.

The skin adhesion layer may contain fatty acids such as acetic acid, caprylic acid, pelargonic acid, capric acid, lauric acid, myristic acid, palmitic acid, stearic acid, oleic acid and the like; hydroxyl acids such as glycolic acid, lactic acid, malic acid, tartaric acid, citric acid and the like; keto acids such as levulinic acid and the like; dicarboxylic acids such as fumaric acid, maleic acid and the like; organic bases such as monoethanolamine, diethanolamine, triethanolamine, diisopropanolamine, triisopropanolamine, pyridine, arginine and the like; plant-derived fats and oils such as olive oil, castor oil, coconut oil and the like; animal-derived fats and oils such as liquid lanolin and the like; organic solvents such as methanol, ethanol, straight chain or branched propanol, straight chain or branched butanol, straight chain or branched pentanol, straight chain or branched hexanol, straight chain or branched heptanol, dimethyldecyl sulfoxide, methyloctyl sulfoxide, dimethyl sulfoxide, dimethylformamide, dimethylacetamide, dimethyllaurylamide, methylpyrrolidone, dodecylpyrrolidone, isosorbitol, N-methyl-2-pyrrolidone and the like; surfactants such as polyoxyethylene hydrogenated castor oil derivative (polyoxyethylene hydrogenated castor oil 40, polyoxyethylene hydrogenated castor oil 50, polyoxyethylene hydrogenated castor oil 60 etc.), sodium polyoxyethylene alkyl ether sulfate, sodium alkylnaphthalenesulfonate, polyoxyethylene oleylamine, sodium polyoxyethylene oleyl ether phosphate, polyoxyl stearate, decaglyceryl laurate, polyoxyethylene sorbitan fatty acid ester (polyoxyethylene sorbitan monolaurate, polyoxyethylene sorbitan monopalmitate, polyoxyethylene sorbitan monostearate, polyoxyethylene sorbitan monooleate etc.), sorbitan fatty acid ester, polyoxyethylene fatty acid ester, polyoxyethylene polyoxypropylene glycol, sucrose fatty acid ester, amine oxide, sodium lauryl sulfate and the like; stabilizers such as tocopherol and the like; plasticizers such as lactate (ethyl lactate, cetyl lactate etc.), diisopropyl adipate, phthalate (dibutyl phthalate etc.), diethyl sebacate, triethyl citrate, benzyl acetate and the like; hydrocarbons such as squalane, squalene, liquid paraffin and the like; fatty acid esters such as ethyl oleate, oleyl oleate, isopropyl palmitate, octyl palmitate, isopropyl myristate, isotridecyl myristate, octyldodecyl myristate, ethyl laurate, hexyl laurate, isostearyl laurate and the like; polyhydric alcohol-fatty acid esters such as glycerol-fatty acid ester, propylene glycol-fatty acid ester and the like; polyhydric alcohols such as glycerol, ethylene glycol, diethylene glycol, propylene glycol, dipropylene glycol, tripropylene glycol, triethylene glycol, polyethylene glycol, 1,3-propanediol, 1,3-butanediol, polypropylene glycol and the like; straight chain aliphatic alcohol such as 1-octanol, 1-dodecanol, 1-tetradecanol, 1-hexadecanol, 1-octadecanol, 1-eicosanol, 1-docosanol, oleyl alcohol, cetostearyl alcohol and the like; an oil-soluble additive such as branched chain aliphatic alcohols (e.g., 2-hexyl-1-decanol, 2-hexyl-1-dodecanol, 2-octyl-1-dodecanol, 2-hexyl-1-tetradecanol, lanolin alcohol, isostearyl alcohol and the like), cholesterol, phytosterol, ethoxylated stearyl alcohol, hydrogenated rapeseed oil alcohol, α-olefin oligomer, silicone oil and the like, as long as the characteristics of the present invention are not impaired. One kind of these additives may be used alone or two or more kinds thereof may be used in combination.

The skin adhesion layer can also contain, for example, tackifiers such as rosin resin, polyterpene resin, coumarone-indene resin, petroleum resin, terpene-phenol resin, xylene resin and the like, as long as the characteristics of the present invention are not impaired.

When the transdermal absorption preparation of the present invention is a transdermal absorption preparation having a skin adhesion layer laminated on the plaster layer, the plaster layer and the skin adhesion layer may be separately preserved until the transdermal absorption preparation is adhered to the skin surface, and the skin adhesion layer may be laminated on the plaster layer and used when the transdermal absorption preparation is adhered to the skin surface.

A release liner may be laminated on the adhesive face to protect an adhesive face of the plaster layer or skin adhesion layer during preservation of the transdermal absorption preparation.

While the above-mentioned release liner is not particularly limited, glassine, polyethylene, polypropylene, polyester (e.g., poly(ethylene terephthalate) etc.), polystyrene, aluminum film, foamed polyethylene film or foamed polypropylene film and the like, or a laminate of those selected therefrom, or those further subjected to silicone processing or emboss processing and the like.

The thickness of the release liner is generally 10 μm-200 μm, preferably 25 μm-100 μm.

Of the above-mentioned release liners, those composed of a polyester (particularly, poly(ethylene terephthalate)) resin is preferable from the aspects of barrier property and cost. In this case, those having a thickness of about 25 μm-100 μm are more preferable from the aspect of handling property.

As the release liner, one having an interface side with the plaster layer or skin adhesion layer subjected to an easy release treatment is preferable to facilitate detachment of the plaster layer or the skin adhesion layer.

The easy release treatment can be performed using a known method. For example, a treatment to form an easy release-treated layer by using a mold release agent containing a curable silicone resin as a main component by a coating method such as bar coating, gravure coating and the like can be mentioned.

The thickness of the easy release-treated layer is preferably 0.01 μm-5 μm to ensure release property and uniformity of the coated film. The thickness of the release liner having an easy release-treated layer is generally 10 μm-200 μm, preferably 25 μm-100 μm, from the aspect of handling property.

The release liner having a laminate (cover) of a plaster layer or a skin adhesion layer preferably has an extended part protruding from the periphery of the plaster layer or the skin adhesion layer. The length of the extended part (length protruding from the periphery of the plaster layer or skin adhesion layer) is preferably about 0.5 mm-10 mm, more preferably about 1 mm-3 mm.

It is preferable to form a sheet of the transdermal absorption preparation of the present invention and provide same as a transdermal absorption preparation sheet (hereinafter to be also referred to as the "transdermal absorption drug sheet" in the present specification).

The transdermal absorption drug sheet of the present invention may be provided as a tape preparation (e.g., plaster; etc.), cataplasm and the like.

The production method of the transdermal absorption preparation of the present invention is not particularly limited, and a generally known production method can be used. For example, a drug, a polymer having a glass transition temperature of 30-200° C. and a pH adjuster are kneaded with heating using a twin screw hot melt extruder and the like and, after the drug is uniformly dispersed, an appropriate amount of the molten mixture is placed on the release liner or a substrate or a cover material and compression molded using a heat pressing machine, whereby a transdermal absorption preparation can also be formed. Alternatively, the above-mentioned molten mixture may be formed using a T-die into a sheet on a release liner to form a transdermal absorption preparation.

EXAMPLES

The present invention is explained in detail by the Examples. In the following, "part" means "part by weight" and "%" means "wt %" unless particularly indicated.

<Polymer A>

Under an inert gas atmosphere, 2-ethylhexyl acrylate (55 parts), acrylic acid (5 parts), N-hydroxyethylacrylamide (5 parts), N-vinyl-2-pyrrolidone (40 parts), and azobisisobutyronitrile (0.2 part) were subjected to solution polymerization in ethyl acetate at 60° C. to give an ethyl acetate solution of an acrylic copolymer. Thereafter, ethyl acetate was removed to give polymer A (solid, glass transition temperature: −26.9° C.)

The compositions and composition ratios of the transdermal absorption preparations of Examples 1-13 and Comparative Examples 1-3 are shown in Table 1.

TABLE 1

|  |  | Example |  |  |  |  |  |  |  |  |  |  |  |  | Comparative Example (part by weight) |  |  |
|---|---|---|---|---|---|---|---|---|---|---|---|---|---|---|---|---|---|
|  |  | 1 | 2 | 3 | 4 | 5 | 6 | 7 | 8 | 9 | 10 | 11 | 12 | 13 | 1 | 2 | 3 |
| drug | PGL | 35 | 35 | 35 | 35 | 35 | 35 | 35 | 22 | 35 | 35 | 11 | 35 | 35 | 35 | 50 | 22 |
| polymer | L100-55 | 15 | 15 | 15 | 15 | 15 | 15 | 15 | 20 | 5 | 5 | — | 8 | 8 | 15 | 15 | — |
|  | S100 | — | — | — | — | — | — | — | — | 10 | — | — | — | — | — | — | — |
|  | L100 | — | — | — | — | — | — | — | — | — | 10 | — | — | — | — | — | — |
|  | RLPO | — | — | — | — | — | — | — | — | — | — | 60 | — | — | — | — | — |
|  | HPC-M | — | — | — | — | — | — | — | — | — | — | — | 7 | — | — | — | — |
|  | Pullulan | — | — | — | — | — | — | — | — | — | — | — | — | 7 | — | — | — |
|  | polymer A | — | — | — | — | — | — | — | — | — | — | — | — | — | — | — | 20 |
| pH adjuster | CA | 25 | 25 | 37 | 25 | 31 | 27 | 24 | — | 25 | 25 | — | 27 | 27 | 33 | 25 | — |
|  | OA | — | — | — | — | — | — | — | 38 | — | — | 20 | — | — | — | — | 39 |
|  | MIPA | 25 | — | — | — | — | — | — | — | — | — | — | — | — | — | — | — |
|  | DIPA | — | — | — | — | — | — | — | — | 25 | 25 | 9 | — | — | — | 10 | 19 |
|  | TIPA | — | — | — | — | — | — | 26 | — | — | — | — | — | — | — | — | — |
|  | MEA | — | — | 13 | — | — | — | — | — | — | — | — | — | — | — | — | — |
|  | DEA | — | 25 | — | — | 19 | — | — | — | — | — | — | — | — | — | — | — |
|  | TEA | — | — | — | 25 | — | 23 | — | 20 | — | — | — | 23 | 23 | 17 | — | — |
| pH of surface of plaster layer |  | 9.86 | 8.48 | 7.57 | 7.40 | 7.18 | 7.11 | 6.78 | 7.16 | 7.31 | 7.50 | 6.90 | 7.06 | 7.09 | 6.61 | 6.21 | 6.87 |

PGL: pregabalin
L100-55: Eudragit L100-55
S100: Eudragit S100
L100: Eudragit L100
RLPO: Eudragit RLPO
HPC-M: hydroxypropylcellulose (manufactured by NIPPON SODA CO., LTD., HPC-M))
Pullulan: pullulan (manufactured by Hayashibara Biochemical Laboratories, Inc.)
CA: capric acid
OA: oleic acid
MIPA: monoisopropanolamine
DIPA: diisopropanolamine
TIPA: triisopropanolamine
MEA: monoethanolamine
DEA: diethanolamine
TEA: triethanolamine According to the composition and composition ratio shown in Table 1, a pH adjuster, a polymer and a drug were kneaded using a twin screw hot melt extruder while heating to 90° C. and extruded to give a mixture. An appropriate amount of the aforementioned mixture was placed on a peel treated surface of a poly(ethylene terephthalate) (PET) release liner (thickness: 75 μm), a non-woven fabric side of a laminate substrate of a PET-film (thickness: 2 μm)/PET non-woven fabric (basis weight: 12 g/m$^2$) was placed to cover the mixture and compression molded by a heat press (temperature: 90° C., compressive force: 400 kPa) into a sheet with a thickness of the mixture of 200 μm to give a transdermal absorption preparation.

(1) pH of Surface of Plaster Layer

The release liner of the transdermal absorption preparation was removed by detaching, the probe of a pH meter (manufactured by Horiba, Ltd., D-72) was slightly wetted and pressed against the exposed surface of the plaster layer, and 20 pH of the surface of the plaster layer was measured. The results are shown in Table 1.

(2) Permeability Evaluation

To a stratum corneum layer surface of the skin (intact skin) isolated from the abdomen of a hairless mouse was adhered the transdermal absorption preparation punched out in 6 mmφ and after peeling off the release liner, and the transdermal absorption preparation was fixed by adhering a cover tape (medical tape manufactured by 3M: 1774W) over the preparation. The isolated skin to which the transdermal absorption preparation had been adhered and fixed was set on a flow-through diffusion cell device, the receptor solution was sampled at every given time, and the skin permeation amount 24 hr later was calculated. As the receptor solution, phosphate buffered saline at 32° C. was used and the flow was set to about 2.5 mL/h. The concentration of the drug pregabalin in the receptor solution was quantified using "ACQUITY TQD" (manufactured by Waters) by liquid chromatography-tandem mass spectrometry method (LCMSMS) according to "Validation of Pregabalin in Human Plasma by LCMS Method", G. Uma, M. Manimala, M. Vasudevan, S. Karpagam and Deecaraman; International Journal of Research and Development in Pharmacy and Life sciences, 2012, Vol. 1, No. 3, 151-155 and the like.

(3) Drug Dispersibility in Plaster Layer

The release liner was removed from the transdermal absorption preparation, and the exposed plaster layer was observed under a polarization microscope (magnification 500 times). The layer on which the drug crystal was uniformly dispersed was evaluated to have "good" dispersibility, and the layer showing insufficient dispersion was evaluated to have "poor" dispersibility.

The results of the permeability evaluation and drug dispersibility in the plaster layer of the transdermal absorption preparations of Examples 1-13 and Comparative Examples 1-3 are shown in Table 2.

TABLE 2

| | Example | | | | | | | | | | | | | Comparative Example | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 1 | 2 | 3 |
| permeability (μg/cm²/24 h) | 3524 | 3584 | 3945 | 5782 | 4159 | 3841 | 2682 | 5199 | 4103 | 3851 | 1425 | 6895 | 6441 | 739 | 865 | 1633 |
| drug dispersibility | good | good | good | good | good | good | good | good | good | good | good | good | good | good | good | poor |

As shown in Table 2, it was found that the transdermal absorption preparations of Examples 1-13 of the present invention afforded good skin permeability, and the drug dispersibility in the plaster layer was also fine.

In contrast, the transdermal absorption preparations of Comparative Examples 1 and 2 showed a certain level of skin permeability but the level was not sufficient. In addition, the transdermal absorption preparation of Comparative Example 3 afforded good skin permeability but the drug dispersibility in the plaster layer was insufficient.

INDUSTRIAL APPLICABILITY

As described in detail above, the present invention can provide a transdermal absorption preparation that shows superior skin permeability of a drug and can uniformly disperse and maintain the drug in the preparation.

The transdermal absorption preparation of the present invention can be preferably provided as a sheet preparation.

This application is based on a patent application No. 2018-013614 filed in Japan, the contents of which are incorporated in full herein.

The invention claimed is:

1. A transdermal absorption preparation comprising a plaster layer containing pregabalin, a polymer having a glass transition temperature of 50° C.-200° C., and a pH adjuster, wherein
    a surface of the plaster layer has a pH within a range of 6.7-10.0,
    the plaster layer does not contain a polymer other than the polymer having a glas transition temperature of 50° C.-200° C., and
    the polymer having a glass transition temperature of 50° C.-200° C. is at least one member selected from the group consisting of methacrylic acid-ethyl acrylate copolymer, methacrylic acid-methyl methacrylate copolymer, methyl methacrylate-ethyl acrylate- trimethylammonioethyl methacrylate chloride copolymer, hydroxypropylcellulose, and pullulan.

2. The transdermal absorption preparation according to claim 1, wherein the pH adjuster is an organic acid and/or an organic base.

3. The transdermal absorption preparation according to claim 2, wherein the organic acid is a fatty acid having 4-20 carbon atoms and the organic base is an aliphatic amine having 4-12 carbon atoms.

4. The transdermal absorption preparation according to claim 1, further comprising a substrate or a cover material, or a substrate and a cover material laminated on the plaster layer.

5. The transdermal absorption preparation according to claim 1, further comprising a skin adhesion layer.

6. The transdermal absorption preparation according to claim 1, which is in the form of a sheet.

7. The transdermal absorption preparation according to claim 1, wherein the polymer having a glass transition temperature of 50° C.-200° C. is at least one member selected from the group consisting of hydroxypropylcellulose and pullulan.

8. The transdermal absorption preparation according to claim 1, wherein the polymer having a glass transition temperature of 50° C.-200° C. is at least methacrylic acid-ethyl acrylate copolymer.

9. The transdermal absorption preparation according to claim 1, wherein the polymer having a glass transition temperature of 50° C.-200° C. is at least methacrylic acid-methyl methacrylate copolymer.

10. The transdermal absorption preparation according to claim 1, wherein the polymer having a glass transition temperature of 50° C.-200° C. is at least methyl methacrylate-ethyl acrylate-trimethylammonioethyl methacrylate chloride copolymer.

11. The transdermal absorption preparation according to claim 1, wherein the polymer having a glass transition temperature of 50° C.-200° C. is at least hydroxypropylcellulose.

12. The transdermal absorption preparation according to claim 1, wherein the polymer having a glass transition temperature of 50° C.-200° C. is at least pullulan.

* * * * *